United States Patent [19]

Sachs

[11] Patent Number: 4,786,741
[45] Date of Patent: Nov. 22, 1988

[54] PREPARATION OF ALKYLENE CARBONATES

[75] Inventor: Howard M. Sachs, Riverdale, N.Y.

[73] Assignee: Scientific Design Company, Inc., Little Ferry, N.J.

[21] Appl. No.: 441,191

[22] Filed: Nov. 15, 1982

[51] Int. Cl.[4] .......................................... C07D 317/12
[52] U.S. Cl. ..................................................... 549/230
[58] Field of Search ........................................ 549/230

[56] References Cited

U.S. PATENT DOCUMENTS

| | | | |
|---|---|---|---|
| 2,667,497 | 1/1954 | Cline | 549/230 |
| 2,766,258 | 10/1956 | Malkemus | 549/230 |
| 2,773,070 | 12/1956 | Lichtenwalter et al. | 549/230 |
| 2,773,881 | 12/1956 | Dunn | 549/230 |
| 2,993,908 | 7/1961 | Milliken et al. | 549/230 |
| 2,994,704 | 8/1961 | Crosby et al. | 549/230 |
| 2,994,705 | 8/1961 | Crosby et al. | 549/230 |
| 3,535,341 | 10/1970 | Emmons et al. | 549/230 |
| 3,629,343 | 12/1971 | Levin et al. | 260/63 SE |
| 3,922,314 | 11/1975 | Cocuzza et al. | 260/63 SE |
| 4,160,116 | 7/1979 | Mieno et al. | 568/867 |
| 4,233,221 | 11/1980 | Raines | 549/230 |
| 4,314,945 | 2/1982 | McMullen et al. | 549/230 |

FOREIGN PATENT DOCUMENTS

| | | |
|---|---|---|
| 55-122776 | 9/1980 | Japan . |
| 56-45426 | 4/1981 | Japan . |
| 1177877 | 1/1970 | United Kingdom . |
| 1485925 | 9/1977 | United Kingdom . |

*Primary Examiner*—Glennon H. Hollrah
*Assistant Examiner*—Mark William Russell
*Attorney, Agent, or Firm*—Kenneth H. Johnson

[57] ABSTRACT

Alkylene carbonates, particularly ethylene carbonate, are prepared by the reaction of an alkylene oxide with carbon dioxide in the presence of a catalyst at temperatures ranging upwards from 20° C., particularly temperatures above about 90° C., preferably 90°–170° C. The conversion of alkylene oxide to alkylene carbonate can be carried out in the presence of water while minimizing the undesirable hydrolysis of the carbonate to the corresponding alkylene glycol and formation of higher glycols. This is achieved by maintaining the water to alkylene oxide molar ratio and the carbon dioxide to alkylene oxide ratio within the stated limits and adjusting the carbon dioxide partial pressure to provide the desired selectivity to alkylene carbonate.

10 Claims, No Drawings

PREPARATION OF ALKYLENE CARBONATES

PRIOR ART

The invention relates to a process for the preparation of alkylene carbonates by the reaction of the corresponding alkylene oxide with carbon dioxide. Such reactions are well known in the art. Alkylene carbonates are useful as solvents or as a source of the corresponding glycols. They are considered to be intermediates in the reaction of ethylene oxide with water to form ethylene glycol in the presence of carbon dioxide, while avoiding the inefficiency associated with the conventional hydration process.

Several processes have been disclosed for a single step hydration of alkylene oxides to glycols in the presence of a catalyst and carbon dioxide. Such processes are said to make possible the reduction in the amount of water used. The removal of excess water is a major expense in the conventional hydration process. The carbon dioxide is not consumed in the process, but it has been suggested that the hydration proceeds via the alkylene carbonate as an intermediate compound.

U.S. Pat. No. 3,922,314 discloses a process for the hydration of ethylene oxide to ethylene glycol which uses no catalyst, but operates with an aqueous ethylene oxide solution containing at least 8 wt % ethylene oxide and at least 0.1 wt % carbon dioxide.

A catalytic process is described in British Patent No. 1,177,877 (or U.S. Pat. No. 3,629,343). Alkylene oxides are hydrated to the glycols at temperatures of 80°–220° C. and pressures of 10–180 atmospheres in the presence of a halide catalyst. Preferred are alkali metal or quaternary ammonium halides, particularly bromides and iodides. Alkali metal hydroxides, carbonates, or bicarbonates were said to be beneficial.

A similar process is discussed in U.S. Pat. No. 4,160,116 where quaternary phosphonium halides, preferably the iodides and bromides were used to catalyze the hydration of alkylene oxides in the presence of carbon dioxide. The temperature is 50°–200° C. and the pressure 3–50 $kg/cm^2$.

Still another such process is disclosed in published Japanese Patent Application No. 81-45426, in which molybdenum and/or tungsten compounds are combined with known catalysts such as alkali metal halides, quaternary ammonium or phosphonium salts, organic halides, and organic amines. The reaction is stated to be carried out at 20°–250° C. and 0–30 $kg/cm^2$ gauge.

The formation of alkylene carbonates, as opposed to the hydration of alkylene oxides to glycols, takes place in the prior art to be discussed with no water present. Catalysts and reaction conditions similar to those described above for the hydration of alkylene oxides have been disclosed to be useful.

In U.S. Pat. No. 2,667,497 magnesium or calcium halides were used at 150°–250° C. and 500–2000 psi to produce alkylene carbonates from the corresponding oxides.

U.S. Pat. No. 2,766,258 discloses the use of quaternary ammonium hydroxides, carbonates, and bicarbonates to catalyze the reaction of alkylene oxides with carbon dioxide. The reaction was carried out at temperatures between 100°–225° C. and pressures of 300–5000 psig.

The quaternary ammonium halides were used by the patentees in U.S. Pat. No. 2,773,070 at temperatures of 100°–225° C. and pressures greater than 300 psi.

Amines were the catalyst used for the reaction by the patentees in U.S. Pat. No. 2,773,881. The reaction was carried out at 100°–400° C. and more than 500 psi.

Three patents issued to the same assignee, i.e. U.S. Pat. Nos. 2,994,705; 2,994,704; and 2,993,908 disclose substantially the same conditions, 93°–260° C. and 8–212 $kg/cm^2$ gauge, with organic phosphonium halides, organic sulfonium halides, and urea hydrohalides given as catalysts for the preparation of alkylene carbonates from the corresponding oxirane compound.

Hydrazine or a halide salt thereof was used to catalyze the reaction by the patentees in U.S. Pat. No. 3,535,341 at temperatures of 100°–250° C. An anion exchange resin containing quaternary ammonium groups was disclosed in U.S. Pat. No. 4,233,221 as useful for vapor-phase reaction.

Organic antimony halides were shown in published Japanese patent application No. 80-122,776 to make possible the formation of alkylene carbonates, at room temperature to 120° C., in a water-free mixture.

In commonly-assigned U.S. patent application Ser. No. 326,447, filed Dec. 2, 1981, it was shown that the reaction of alkylene oxides to the corresponding carbonates can be carried out with known catalysts at lower temperatures than heretofore used in the art and even in the presence of substantial amounts of water. The hydrolysis of the carbonates to glycols can be minimized and the principal product is the carbonate. I have now found that higher temperatures than were previously shown to be useable may be employed, without producing large amounts of glycols, particularly higher glycols provided that the molar ratio of carbon dioxide to alkylene oxide is maintained above about 1/1 and the partial pressure of carbon dioxide is above a preselected value.

SUMMARY OF THE DISCLOSURE

Alkylene oxides may be reacted with carbon dioxide to form alkylene carbonates in the presence of an effective amount of suitable catalysts at temperatures upwards from 20° C., particularly above 90° C., preferably 90° to 170° C. and in the presence of water, when the molar ratio of carbon dioxide to alkylene oxide is at least 1/1 and the partial pressure of carbon dioxide is sufficient to provide the desired selectivity to alkylene carbonate. The pressure at which the reaction is carried out is in the range of about 10–200 $kg/cm^2$ gauge, preferably 30 to 80 $kg/cm^2$ gauge. Suitable catalysts include a member or members of the group consisting of quaternary organic ammonium and phosphonium halides, organic sulfonium halides, and organic antimony halides, particularly methyl triphenyl phosphonium iodide, tetraethyl ammonium bromide, and tetraphenyl antimony bromide. The corresponding carboxylates may also be used. The quantity of catalyst used is generally up to about 0.10 mols per mol of alkylene oxide, preferably 0.001 to 0.02.

Contrary to previous expectations, water may be present in substantial amounts, even exceeding those used in prior art hydration processes, since the formation of large amounts of glycol, and particularly the higher glycols, is avoided by maintaining the molar ratio of carbon dioxide to alkylene oxide above 1/1 and the partial pressure of carbon dioxide is adjusted to provide the selectivity to alkylene carbonate desired.

Useful mol ratios of water to alkylene oxide are above about 0.01/1 and preferably from about 0.1/1 to about 4/1, most preferably from 0.1/1 to 2/1, although higher amounts of water are not excluded. Adding water also increases the rate of carbonate formation.

DESCRIPTION OF THE PREFERRED EMBODIMENTS

Heretofore, those familiar with the reaction of alkylene oxides with carbon dioxide to form alkylene carbonates have carried out the reaction at temperatures generally in the range of 100°–300° C., particularly about 150°–225° C. Although it was not generally discussed in detail, it will be seen from prior art disclosures that the reaction was carried out in the practical absence of water. For Example, in U.S. Pat. No. 4,233,221 the reactants were dried by condensation of water after compression so that the moisture level of the reactant gases was quite low, estimated to be about 0.2 mol percent. Since the hydrolysis of carbonates was known to take place at elevated temperatures and with catalysts also useful for the direct hydrolysis of alkylene oxides to glycols, it seems probable that prior workers in the art avoided water if only the carbonate was to be produced. Otherwise, hydrolysis to glycol could be expected.

Previously, it was disclosed in U.S. application Ser. No. 326,447 that when the reaction of alkylene oxides with carbon dioxide is undertaken at temperatures substantially lower than taught by the prior art, that the presence of water can be not only tolerated, but actually may be beneficial in some instances. Alkylene carbonates can be prepared with minimal losses by hydrolysis to the glycols. Such a process has application to a stream combining carbon dioxide, ethylene oxide, and water obtained by extraction of ethylene oxide from a dilute aqueous solution with near-critical or supercritical carbon dioxide. However, I have now discovered that higher temperatures, i.e. above 90° C., may be used, still without formation of large amounts of glycols, especially the higher glycols, provided that the molar ratio of carbon dioxide to alkylene oxide is maintained above about 1/1 and the partial pressure of carbon dioxide is sufficient to provide the desired selectivity to the alkylene carbonate.

The reaction may be carried out at a wide range of temperatures, especially 90° to 170° C. Lower temperatures disclosed in the commonly-assigned application may be used as well, but are not preferred since the rate of alkylene carbonate formation is higher at temperatures above 90° C.

Total pressure is not an especially critical variable in the reaction. Typically, it will be in the range of about 10–200 kg/cm² gauge. However, the partial pressure of carbon dioxide has been found to be very important.

The molar ratio of carbon dioxide to alkylene oxide must be at least about 1/1 and may range from 1/1 to 100/1. Usually a ratio greater than 1/1 would be selected, preferably 1/1 to 10/1. Where the process of the invention is associated with the extraction of alkylene oxide by (near) super-critical carbon dioxide the ratio may be as high as 40/1–60/1.

It is of particular importance that water need not hydrolyze alkylene carbonates to the glycols, particularly the higher glycols, under conditions found suitable for the process of the invention. At temperatures above about 90° C., the amount of glycols produced was expected in the earlier application to increase until eventually the process would no longer produce carbonates, but glycols instead, as disclosed in the patents mentioned earlier. I have now found that the formation of glycols can be restrained by providing sufficient carbon dioxide. One skilled in the art would not have predicted such a result because with water present and at the temperatures here employed, the prior art teaches that water would hydrolyze the alkylene oxide to glycol. It was thought that the reaction proceeded via formation of the alkylene carbonate as an intermediate compound. For example see U.S. Pat. Nos. 4,237,324 and 4,117,250, along with U.S. Pat. No. 3,629,343 to Levin, et al. The alkylene carbonate was apparently not observed in any significant quantities, since quantitative yields of glycols were reported.

The amount of water which can be tolerated, has some relation to the other process conditions and the selectivity to alkylene carbonate formed. Amounts in excess of those useful for the direct hydration of alkylene oxides to glycols have been demonstrated at lower temperatures, as will be seen in subsequent examples. At temperatures above about 90° C., particularly 90°–170° C., amounts of water up to about mol ratios of 4/1 based on alkylene oxide are preferred, most preferably 0.1/1 to 2/1. Th presence of water has a beneficial effect on the rate of carbonate reaction, contrary to what might be expected. This effect may be more pronounced in association with certain catalysts, particularly those in which the bond between the halide atom and the rest of the molecule is ionic, rather than covalent in nature, such as with the preferred quaternary phosphonium halides.

The catalysts found useful in the process of the invention include many of those known in the art. Broad classes of compounds which may be useful include one or more members of the group consisting of organic quaternary ammonium or phosphonium halides, organic sulfonium halides, and organic antimony halides. The corresponding carboxylates also may be used. Examples of compounds which may be employed are the following ammonium compounds, tetraethyl ammonium bromide, and tetra ethyl ammonium iodide. Specific phosphonium compounds include methyl triphenyl phosphonium iodide and methyl triphenyl phosphonium bromide. Sulfonium compounds may include trimethyl sulfonium iodide and trimethyl sulfonium bromide. Antimony compounds have been found quite effective when no water is present, but appear to be adversely affected when water is included. Typical compounds are tetraphenyl antimony bromide and triphenyl antimony dichloride. Particularly preferred catalysts when water is present are methyl triphenyl phosphonium iodide and tetraethyl ammonium bromide. Of the halides, bromides and iodides are preferred.

The amount of catalyst will be similar to that used in other processes, up to about 0.1 mols of the catalyst per mol of alkylene oxide may be used, preferably 0.001–0.02 mols per mol, although larger or smaller amounts are not intended to be excluded.

While other workers in the field have indicated that relatively high temperatures of 100° C. or higher would be used either to form alkylene carbonates when no water was present, or alkylene glycols when water was available to hydrolyze alkylene oxides, the present process employs temperatures ranging upward from about 20° C. preferably above 90° C., particularly 90°–170° C.

The reaction to form carbonates may be carried out in the presence of substantial amounts of water. At higher temperatures typical of the prior art, glycols would be expected when water is present and, in fact, this is the basis for several processes as previously discussed. As will be seen, even when operating at relatively high temperatures, it is possible to minimize hydrolysis and to form carbonates instead, by control of the molar ratio of carbon dioxide to alkylene oxide and the partial pressure of carbon dioxide.

The first five examples which follow are repeated from co-pending and commonly-assigned U.S. application Ser. No. 326,447 and illustrate formation of alkylene carbonates at temperatures below 90° C.

EXAMPLE 1

Operating below 90° C. without water present

A sample of the catalyst being tested is introduced to a 130 cc bomb produced by the Parr Instrument Company. Samples of ethylene oxide and carbon dioxide are charged at −78° C. by immersing the bomb in a dry-ice/acetone bath. The bomb is then closed and placed in a 36° C. bath so that the internal temperature of the bomb is increased to 30° C. and the reaction proceeds. Agitation is via a magnetically driven disk. After a suitable period of time, the bomb is removed from the bath and the contents analyzed. The results of a number of such tests are shown in Table A below.

TABLE A

| Test No. | Feed, millimols EO* | Feed, millimols $CO_2$ | Catalyst, gms*** | Bath °C. | Time, hrs | Max. Pressure $kg/cm^2$ gauge | EO* Conv. % | EC** Sel. % |
|---|---|---|---|---|---|---|---|---|
| 1 | 13.6 | 681 | a 0.1456 | 36 | 19.5 | 28.1 | 51.7 | — |
| 2 | 13.6 | 681 | b 0.4385 | 36 | 19.5 | 29.5 | 55 | 16 |
| 3 | 18.2 | 681 | c 0.3654 | 32 | 19.5 | 18.3 | 94 | 88.2 |
| 4 | 15.9 | 681 | d 0.3064 | 37 | 18.5 | 15.5 | 37.7 | — |
| 5 | 18.2 | 1022 | e 0.3881 | 38 | 19.5 | 30.6 | 51.1 | — |
| 6 | 22.7 | 1022 | f 0.2406 | 38 | 19.5 | 78.1 | 77.9 | 50.4 |

*EO = ethylene oxide
**EC = ethylene carbonate
***a = trimethyl sulfonium iodide
b = methyl triphenyl phosphonium iodide
c = tetraphenyl antimony bromide
d = triphenyl antimony dichloride
e = methyl triphenyl phosphonium bromide
f = tetraethyl ammonium bromide It has been discovered that water may be present without formation of significant amounts of glycols, provided that the temperature is sufficiently low. Surprisingly, it has been found that water has a beneficial effect on the selectivity to the carbonate with some catalysts, while with others the selectivity appears to be suppressed.

EXAMPLE 2

Effect of Water on Catalysts

The procedure of Example 1 is followed except that varying amounts of water are introduced to the Parr bomb, with the following results.

TABLE B

| Test No. | Feed, millimols EO | Feed, millimols $CO_2$ | Feed, millimols $H_2O$ | Catalyst, gms* | Bath °C. | Time, hrs | Max. Pres. $kg/cm^2$ gauge | EO Conv. % | EC Sel. % |
|---|---|---|---|---|---|---|---|---|---|
| 7 | 19.3 | 1022 | — | c 0.5507 | 33 | 19.5 | 27.8 | 91.1 | 88.5 |
| 8 | 18.2 | 1022 | 10 | c 0.5466 | 34 | 19.5 | 27.4 | 95.6 | 47.1 |
| 9 | 20.4 | 1022 | 5 | b 0.4380 | 37 | 21 | 44.3 | 86 | 35 |
| 10 | 20.4 | 1022 | 20 | b 0.4227 | 37 | 21 | 42.5 | 92 | 47.4 |
| 11 | 20.4 | 1022 | 40 | b 0.4319 | 37 | 21 | 43.2 | 93 | 63 |
| 12 | 22.7 | 1022 | 80 | b 0.4365 | 37 | 21 | 41.1 | 83.8 | 76 |

*c = tetraphenyl antimony bromide
b = methyl triphenyl phosphonium iodide

The data of Table B show that the presence of water appears to have no recognizable effect on the overall conversion of ethylene oxide, the selectivity to ethylene carbonate is reduced when catalyst "c" is used, while when catalyst "b" is employed the selectivity to ethylene carbonate is surprisingly improved. Catalyst "c" would be more suitable for a reaction system in which the amount of water present is not large. Note that the ratio of water to ethylene oxide is about 0.55/1 compared to the theoretical ratio of 1/1 for the hydrolysis reaction. Catalyst "b" appears less effective when no water is present (see test 2) but its performance is enchanced when water is used. Note that the ratios for this catalyst shown reach nearly 4/1 water/EO.

Although the process of the invention is particularly useful in connection with the formation of ethylene carbonate, it is more widely applicable to other oxirane compounds, as will be seen in the following example.

EXAMPLE 3

Formation of propylene carbonate

A sample of the catalyst being tested and water (if used) is introduced to a 130 cc Parr bomb. Samples of propylene oxide and carbon dioxide are charged at −78° C. by immersing the bomb in a dry-ice/acetone bath. The bomb is then closed and placed in a 36° C. bath so that the internal temperature of the bomb is increased to 30° C. and the reaction proceeds. After a suitable period of time, the bomb is removed from the bath and the contents analyzed. The results of a number of such tests are shown in Table C below.

TABLE C

| Test No. | Feed, millimols | | | Catalyst, gms*** | Bath °C. | Time, hrs | Max. Pres. kg/cm² gauge | PO Conv. % | PC** Sel. % |
|---|---|---|---|---|---|---|---|---|---|
| | PO* | CO₂ | H₂O | | | | | | |
| 13 | 20.3 | 1022 | — | a 0.5511 | 35 | 21 | 42.6 | 96.2 | 90.3 |
| 14 | 20.6 | 1022 | — | b 0.4385 | 36 | 21 | 34.2 | 60.2 | 25.4 |
| 15 | 20.2 | 1022 | — | c 0.2401 | 36 | 21 | 56.1 | 85.0 | 58.3 |
| 16 | 20.4 | 1022 | 5 | b 0.4382 | 36 | 21 | 47.3 | 88.2 | 34.6 |
| 17 | 20.6 | 1022 | 20 | b 0.4378 | 36 | 21 | 52.8 | 89.7 | 56.4 |
| 18 | 20.1 | 1022 | 40 | b 0.4386 | 36 | 21 | 54.2 | 87.4 | 68.3 |
| 19 | 20.4 | 1022 | 80 | b 0.4391 | 36 | 21 | 62.1 | 91.4 | 82.3 |

*PO = propylene oxide
**PC = propylene carbonate
***a = tetraphenyl antimony bromide
b = methyl triphenyl phosphonium iodide
c = tetraethyl ammonium bromide

EXAMPLE 4

Formation of 1,2 butylene carbonate

The experimental procedure of Example 3 was followed with 1,2-butylene oxide charged in lieu of propylene oxide. The results of a number of such tests are shown in Table D below.

TABLE D

| Test No. | Feed, millimols | | | Catalyst, gms*** | Bath °C. | Time, hrs | Max. Pres. kg/cm² gauge | BO Conv. % | BC** Sel. % |
|---|---|---|---|---|---|---|---|---|---|
| | BO* | CO₂ | H₂O | | | | | | |
| 20 | 20.4 | 1022 | — | a 0.5513 | 36 | 21 | 44.8 | 92.1 | 87.6 |
| 21 | 20.7 | 1022 | — | b 0.4378 | 36 | 21 | 47.2 | 58.3 | 22.6 |
| 22 | 20.1 | 1022 | — | d 0.2436 | 36 | 21 | 42.6 | 82.0 | 53.2 |
| 23 | 20.1 | 1022 | 5 | b 0.4386 | 36 | 21 | 51.8 | 89.2 | 40.5 |
| 24 | 20.8 | 1022 | 20 | b 0.4392 | 36 | 21 | 43.8 | 91.4 | 59.8 |
| 25 | 20.2 | 1022 | 40 | b 0.4369 | 36 | 21 | 56.2 | 93.4 | 72.8 |
| 26 | 20.6 | 1022 | 80 | b 0.4381 | 36 | 21 | 53.6 | 90.8 | 84.3 |

*BO = 1,2-butylene oxide
**BC = 1,2-butylene carbonate
***a = tetraphenyl antimony bromide
b = methyl triphenyl phosphonium iodide
c = tetraethyl ammonium bromide

EXAMPLE 5

A sample of the catalyst being tested, along with H₂O and solvents (when used) is introduced to a 300 cc electrically heated stainless steel autoclave equipped with impeller agitation produced by Autoclave Engineers, Inc. Samples of ethylene oxide and carbon dioxide are charged at −78° C. while the autoclave is immersed in a dry-ice/acetone bath. The autoclave is then closed and heated to the desired reaction temperature. After a suitable period of time, the autoclave is cooled and the contents analyzed. The results of a number of such tests are shown in Table E below.

The following examples illustrate the process of the invention, demonstrating that, contrary to the prior art it is possible to produce high yields of alkylene carbonates above about 90° C. in the presence of substantial amounts of water and suppressing the formation of the higher glycols.

EXAMPLE 6

Operating above 90° C. with water present

A series of tests were carried out at temperatures above 90° C. with varying amounts of water present. Ethylene oxide, carbon dioxide, water and methyltriphenyl phosphonium iodide dissolved in ethylene carbonate were fed continuously to a one liter, high pressure, agitated, electrically heated auotclave. Both liquid products and unconverted vapors were removed continuously from the autoclave and separated in an external vapor-liquid separator. The composition of both liquid and vapor streams was determined by gas chromatography and the conversion and selectivities were calculated. The results are given in Table F.

TABLE E

| Test No. | Feed, millimols | | | | Bath °C. | Time, hrs | Max. Pres. kg/cm² gauge | EO Conv. % | EC**** Sel. % |
|---|---|---|---|---|---|---|---|---|---|
| | EO* | CO₂ | H₂O | THF** | | | | | |
| 27 | 347 | 1590 | 346 | 1262 | 60 | 4 | 52.0 | 95.6 | 97.0 |
| 28 | 695 | 2794 | 695 | — | 60 | 6 | 104.8 | 95.8 | 90.5 |
| 29 | 1157 | 2113 | 583 | — | 50 | 6 | 57.7 | 98.2 | 95.5 |
| 30 | 349 | 1590 | 350 | 1263 | 70 | 2 | 57.3 | 99.5 | 96.0 |

*EO = ethylene oxide
**THF = tetrahydrofuran
***Each test used 20 grams of methyl triphenyl phosphonium iodide
****EC = ethylene carbonate

TABLE F

| Test No. | Temp. °C. | Mol H$_2$O Mol EO | Mol CO$_2$ Mol EO | Pres. kg/cm$^2$ gauge | Cat. mol on EO | Feed EO mol/hr/l | EO Conv % | EC Sel % | MEG Sel % | DEG Sel % |
|---|---|---|---|---|---|---|---|---|---|---|
| 31 | 130 | 0.27 | 2 | 66 | 0.01 | 6.1 | 95.5 | 99.3 | 0.7 | nil* |
| 32 | 130 | 0.5 | 1.3 | 66 | 0.012 | 6.5 | 99 | 96.5 | 3.5 | nil |
| 33 | 130 | 1.0 | 2.0 | 66 | 0.013 | 6.0 | 99 | 87.5 | 12.5 | nil |
| 34 | 130 | 1.0 | 1.3 | 66 | 0.014 | 6.8 | 99.5 | 93.3 | 6.7 | nil |
| 35 | 130 | 1.9 | 2.0 | 66 | 0.010 | 4.0 | 99 | 74.3 | 23.9 | 1.7 |
| 36 | 130 | 2.0 | 2.0 | 66 | 0.002 | 6.1 | 91 | 66.1 | 30.8 | 3.1 |
| 37 | 170 | 0.25 | 2.0 | 66 | 0.0013 | 6.1 | 97 | 94.7 | 5.3 | nil |
| 38 | 170 | 0.5 | 1.3 | 66 | 0.0022 | 6.4 | 99 | 72.1 | 26.1 | 1.8 |
| 39 | 170 | 0.9 | 1.3 | 66 | 0.002 | 6.8 | 99 | 48.8 | 46.8 | 4.3 |
| 40 | 170 | 1.9 | 2.0 | 66 | 0.0014 | 4.1 | 98 | 14.5 | 72.1 | 13.3 |
| 41 | 170 | 2.0 | 2.0 | 66 | 0.0074 | 4.0 | 98 | — | 92.9 | 7.1 |
| 42 | 90 | 0.25 | 4.0 | 66 | 0.013 | 2.0 | 90 | 94.0 | 5.0 | 0.9 |
| 43 | 50 | 0.11 | 4.0 | 66 | 0.005 | 2.0 | 65 | 94.0 | 4.6 | 1.3 |

*less than 0.25%

From the above table it can be seen that even when operating at temperatures as high as 170° C., that high yields of ethylene carbonate can be obtained, although the amount of water present appears to have a greater effect at 170° C. than at 130° C. In fact, the results of Tests 40 and 41 suggest that conditions can be found where glycol becomes the predominent product. The molar ratio of CO$_2$/EO was greater than 1/1 for each test.

When the CO$_2$/EO molar ratio is below 1/1 distinctly different results are obtained as will be seen from the following examples.

EXAMPLE 7

Effect of CO$_2$/EO ratio

The experimental procedures of Example 6 were repeated to duplicate test 33, except that the pressure was 25 kg/cm$^2$ gauge and the molar ratio of CO$_2$/EO was changed from 2.0 to 0.5. Selectivities of 63.2% to ethylene carbonate (EC) and 36% to ethylene glycol (MEG) were obtained at a CO$_2$/EO ratio of 2, but selectivities of 58% to MEG and 41% to EC were obtained when the CO$_2$/EO ratio was 0.5. Also, the formation of diethylene glycol (DEG) was significant at 1.4% selectivity when the CO$_2$/EO ratio was 0.5, while only 0.8% selectivity to DEG was detected in the products when the CO$_2$/EO ratio was 2. It is concluded that the molar ratio of CO$_2$/EO is an important factor if one wishes to produce alkylene carbonates instead of the corresponding glycol, when an alkylene oxide is reacted with carbon dioxide in the presence of water. In order to achieve such results, the molar ratio of CO$_2$/EO should be at above about 1. The most useful ratio will be selected depending upon the amount of water present and the operating temperature.

EXAMPLE 8

Effect of CO$_2$ partial pressure

The importance of the partial pressure will be seen in the results of tests made in accordance with the methods of Example 6 in which the absolute pressure and the partial pressure were varied.

TABLE G

| Test No. | Temp. °C. | Mol H$_2$O Mol EO | Mol CO$_2$ Mol EO | Press* Total PCO$_2$ | Cat. mol on EO | Feed mol/hr/l EO | EO Conv % | EC Sel % | MEG Sel % | DEG Sel % |
|---|---|---|---|---|---|---|---|---|---|---|
| 44 | 130 | 1.0 | 2.0 | 66/65 | 0.013 | 6.0 | 99 | 87.5 | 12.5 | nil |
| 45 | 130 | 1.0 | 2.0 | 35/34 | 0.010 | 6.2 | 95 | 71.9 | 27.7 | 0.4 |
| 46 | 130 | 1.0 | 2.0 | 25/24.4 | 0.011 | 6.2 | 92 | 63.2 | 36.0 | 0.8 |
| 47 | 130 | 1.0 | 2.0 | 11/10.5 | 0.007 | 6.1 | 82 | 26.8 | 71.5 | 1.6 |
| 48 | 130 | 1.0 | 1.1 | 3.5/1.0 | 0.008 | 6.2 | 66 | 9.8 | 88.4 | 1.8 |

*Total press kg/cm$^2$ gauge; PCO$_2$ = partial press CO$_2$ kg/cm$^2$ abs

It can be seen that if the partial pressure of carbon dioxide is not kept sufficiently high the reaction will produce significant amounts of glycol, which is not desirable if one wants to produce ethylene carbonate instead. Consequently, the temperature, the H$_2$O/EO ratio, and the CO$_2$ partial pressure will be adjusted to produce the selectivity to carbonate desired. For example, if the molar ratio of water to ethylene oxide in the feed were 1/1 and the reaction temperature were 130° C., then the partial pressure of carbon dioxide would be kept at 65 kg/cm$^2$ or even higher to maximize the amount of ethylene carbonate produced.

EXAMPLE 9

Effect of H$_2$O/EO ratio

In another series of tests corresponding to the procedures of Example 6, the amount of water was varied, with the following results:

TABLE H

| Test No. | Temp. °C. | Mol H$_2$O Mol EO | Mol CO$_2$ Mol EO | Pres. kg/cm$^2$ gauge | Cat. mol on EO | Feed mol/hr/l EO | EO Conv % | EC Sel % | MEG Sel % | DEG Sel % |
|---|---|---|---|---|---|---|---|---|---|---|
| 49 | 130 | 0.06 | 2/1 | 66 | 0.010 | 3.6 | 92.0 | 99.8 | 0.2 | — |

TABLE H-continued

| Test No. | Temp. °C. | Mol H₂O Mol EO | Mol CO₂ Mol EO | Pres. kg/cm² gauge | Cat. mol on EO | Feed mol/hr/l EO | EO Conv % | EC Sel % | MEG Sel % | DEG Sel % |
|---|---|---|---|---|---|---|---|---|---|---|
| 50 | 130 | 0.25 | 2/1 | 66 | 0.011 | 4.2 | 97.5 | 89.0 | 11.0 | 0.2 |

Calculation of reaction rate constants indicate that increasing the conversion of ethylene oxide from 92% to 97.5% is equivalent to an increase in reaction rate of about four times. Thus, unexpectedly the addition of water to a dry feed increases the reaction rate markedly while the product of the reaction is still predominantly ethylene carbonate.

I claim:

1. In a process for preparing alkylene carbonate by the reaction of the corresponding alkylene oxide with carbon dioxide in the presence of an effective amount of at least one catalyst selected from the group consisting of organic quaternary ammonium halides, organic quaternary phosphonium halides, organic sulfonium halides, and organic antimony halides and water, the improvement comprising controlling the selectivity of alkylene carbonate and suppressing formation of higher molecular weight glycols to produce high yields of alkylene carbonate by carrying out said reaction at temperatures above about 90° C. with a molar ratio of carbon dioxide to alkylene oxide of at least about 1/1, a water to alkylene oxide molar ratio greater than about 0.01/1, and a carbon dioxide partial pressure sufficient to provide the selectivity to alkylene carbonate desired.

2. The process of claim 1 wherein said reaction temperature is between about 90° C. and about 170° C.

3. The process of claim 1 wherein said molar ratio of water to alkylene oxide is between about 0.01/1 and about 4/1.

4. The process of claim 3 wherein said molar ratio of water to alkylene oxide is between about 0.1/1 and about 2/1.

5. The process of claim 1 wherein said catalyst is an organic quaternary phosphonium halide.

6. The process of claim 5 wherein said catalyst is methyl triphenyl phosphonium iodide.

7. The process of claim 1 wherein said catalyst is up to about 0.10 mols per mol of alkylene oxide.

8. The process of claim 1 wherein said alkylene carbonate is ethylene carbonate.

9. A process for preparing alkylene carbonate from the reaction of the corresponding alkylene oxide with carbon dioxide in the presence of water comprising contacting said carbon dioxide with said alkylene oxide in the molar ratio of at least 1/1 in the presence of at least 0.01 mol of water for each mol of alkylene oxide and in the presence of up to about 0.1 mols of at least one catalyst selected from the group consisting of organic quaternary ammonium halides, organic quaternary phosphonium halides, organic sulfonium halides, and organic antimony halides per mol of alkylene oxide at a temperature above about 90° C. and a total pressure selected to provide a partial pressure of carbon dioxide sufficient to produce more alkylene carbonate than mono alkylene glycol and to minimize production of higher glycols.

10. The process of claim 9 wherein said alkylene oxide is converted to alkylene carbonate with a selectivity of at least 90%.

* * * * *